United States Patent

Benson et al.

[11] Patent Number: 5,092,858
[45] Date of Patent: Mar. 3, 1992

[54] LIQUID GELLING AGENT DISTRIBUTOR DEVICE

[75] Inventors: C. David Benson, Waynesville; Mutlu Karakelle, Spring Valley; Robert A. Taller, Centerville, all of Ohio

[73] Assignee: Becton, Dickinson and Company, Franklin Lakes, N.J.

[21] Appl. No.: 496,475

[22] Filed: Mar. 20, 1990

[51] Int. Cl.[5] .............................. A61M 1/00
[52] U.S. Cl. ........................ 604/319; 604/323
[58] Field of Search .......... 604/326, 333, 336, 319, 604/349, 317; 221/208, 210, 211, 227; 206/204; 5/484

[56] References Cited

U.S. PATENT DOCUMENTS

| | | | |
|---|---|---|---|
| 2,283,867 | 5/1942 | Flosdorf et al. | 312/31 |
| 3,485,404 | 12/1969 | Newton | 604/319 |
| 3,690,320 | 9/1972 | Riely | 604/336 |
| 3,990,872 | 11/1976 | Cullen | 55/274 |
| 4,124,116 | 11/1978 | McCabe, Jr. | 206/204 |
| 4,588,505 | 5/1986 | Walley et al. | 206/204 |
| 4,615,923 | 10/1986 | Marx | 428/35 |
| 4,720,410 | 1/1988 | Lundquist et al. | 206/204 |
| 4,748,069 | 5/1988 | Cullen | 428/195 |
| 4,749,600 | 6/1988 | Cullen et al. | 206/204 |
| 4,840,692 | 6/1989 | Kamstrup-Larsen | 604/368 |
| 4,853,266 | 8/1989 | Cullen | 421/35.7 |

FOREIGN PATENT DOCUMENTS 1362935 4/1964 France .
711186 6/1954 United Kingdom .

Primary Examiner—Randall L. Green
Assistant Examiner—R. Clarke
Attorney, Agent, or Firm—Robert P. Grindle

[57] ABSTRACT

A device is provided for deliberately distributing simultaneously over the entire vertical and/or longitudinal extend of a body of aqueous containing liquid a gelation agent for the rapid containment of contaminated aqueous liquids. The device is an elongated rigid or semi-rigid body for containing an envelope or package of material immediately dissolvable in the aqueous liquids, and which contains the gelling agent prior to liquid exposure. The device includes means for exposure of its content to the liquid, once the device is positioned in or is surrounded by the liquid. The invention contemplates a conventional suction canister having the device positioned therein for receiving contaminated body fluids.

13 Claims, 2 Drawing Sheets

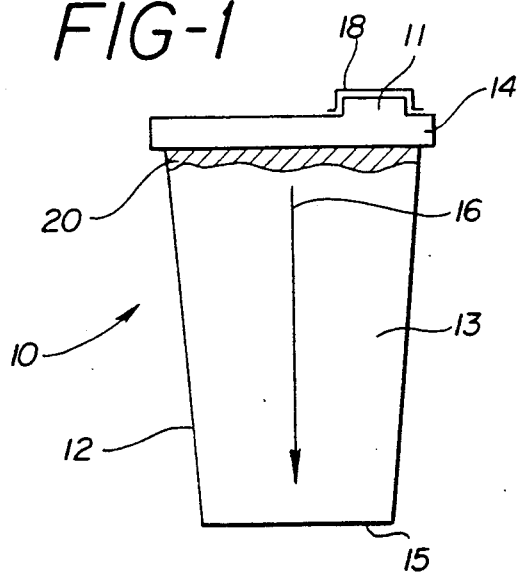
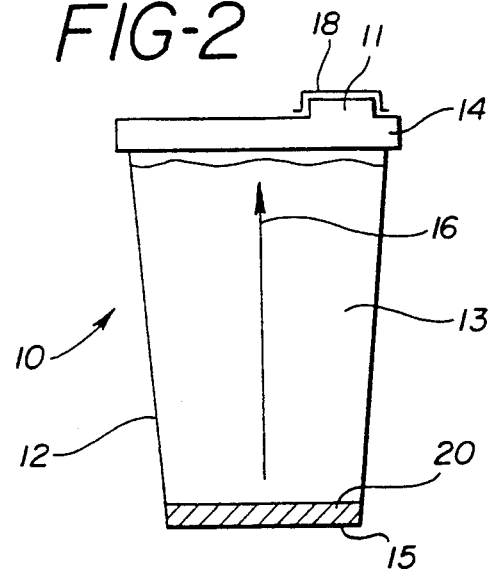
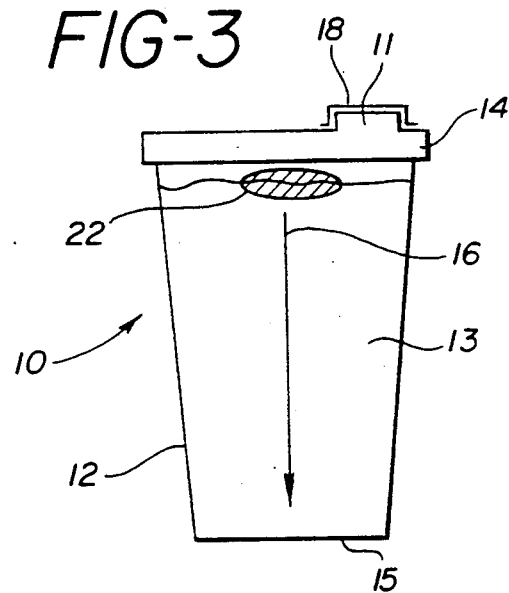
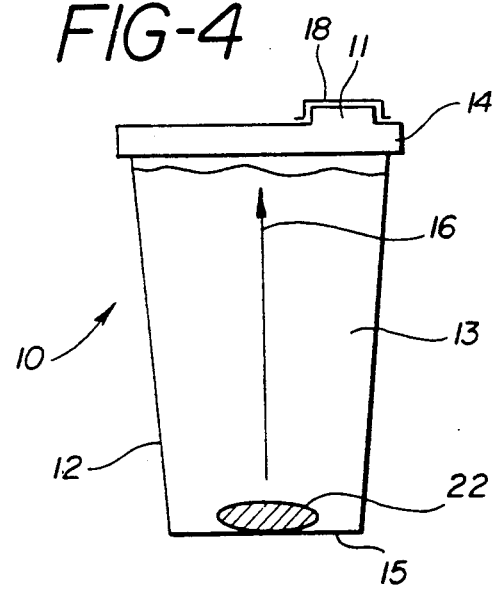
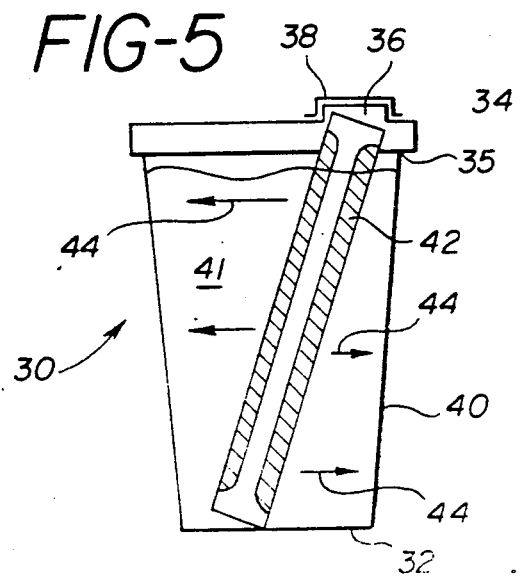
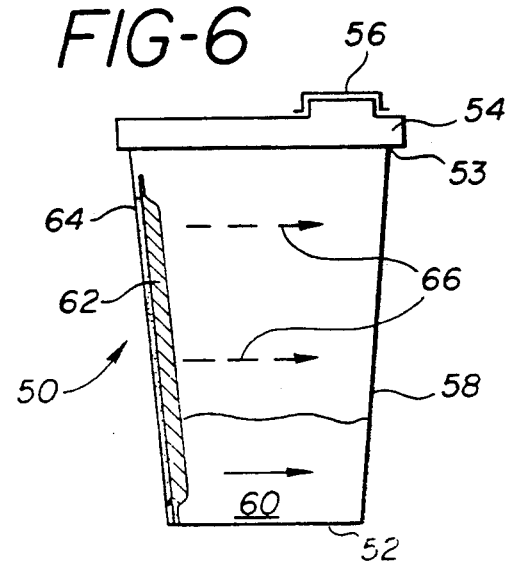

LIQUID GELLING AGENT DISTRIBUTOR DEVICE

BACKGROUND AND DESCRIPTION OF THE INVENTION

The present invention relates to an arrangement for dispensing, simultaneously, over the entire vertical and/or longitudinal extent of a body of fluid a gelling agent which will gel each increment of the body of fluid simultaneously so that it is immediately contained against any spilling or contamination of the handler.

More particularly, this invention relates to such an arrangement which contains a body of gelling agent for insertion and exposure to a body of fluid containing contaminated agents which must be contained immediately following the collection of the body of fluid. In particular, one preferred use of the invention here is the immediate containment of collected fluids in a suction canister used in the operating room for collecting body fluids, which may or may not be contaminated, during an operating procedure. It will be understood by practitioners in the art, however, that the device of the invention may be used for rapid control and gelation of any contained body of aqueous containing fluid.

One of the features of the invention is that the particular arrangement herein reduces the "diffusion length" of the gelling material moving from its contained arrangement to and over the entire body of fluid. Because of this shortened diffusion length, there is, as discussed above, a simultaneous immediate containment of each portion of the liquid being contained.

Suction canisters have been used for a period of years for collecting and containing body fluids during an operation. In general, suction canisters employ a collection system and a vacuum source, such as a pump, to facilitate the drainage procedure. Each canister usually includes a flexible line or hose connected to the vacuum source so that vacuum can be applied to the interior of the canister. Another line extends from the source of body fluids at the patient to the canister. Thus, when a negative pressure gradient is applied across the canister, body fluids are drawn into the canister.

However, due to the fear of contamination of body fluids, including, for example, blood from an AIDS patient or a patient suffering from hepatitis, it has become increasingly important to contain these collected fluids immediately after collection. In removing a container from its collection position and moving it about for disposal, it is relatively easy to spill such liquids and it is to this problem to which this invention is particularly directed.

Arrangements have been made in the past and are well known for gelling fluids. For example, U.S. Pat. Nos. 4,748,069 and 4,749,600 are both directed toward packets containing gelation material for introduction into a shipping container or carton for gelling liquid that leaks from broken bottles, vessels, or other packages. These packets are placed next to a collection vessel for inadvertent leakage containment.

If gelling agents are added to the canister in the form of dissolvable packets, the packets may sink or float and the gelling material itself is exposed only to the fluid immediately adjacent the surface thereof for the first gelling activity. This is a result of the volume configuration constraints of the canister.

Because of this, portions of the active gelling material may become encapsulated within the gel and result in an incomplete or partially gelled liquid matrix. Diffusion of the gel powder through the fluid is restricted initially by the viscosity of the body fluids themselves and later by the viscosity build associated with the gelling process. When the canister is subsequently discarded, the partial or incomplete gelled fluid may leak and/or burst for exposing those individuals who are handling the disposed canisters such as janitors, cleaning personnel, and the like.

A complication associated with pouring the powder into a filled canister is that there is sometimes not sufficient head space between the lid and liquid surface to accommodate the required volume of powder. As a result, the filled canister must be shaken or swirled to mix the powder and avoid the premature encapsulation and clumping. Hospital personnel should not swirl the filled canister because of the chance of leakage around the lid area. In addition, another obvious problem associated with handling free flowing powder is that it can be inadvertently spilled in the operating area as it is being poured into the canister.

Other arrangements in the past include merely pouring or sprinkling the gelation material on the top of the body of fluid in a canister for the gelation thereof. The same problems arise as described above in that that gelling material is not exposed to, for example, the bottom portion of the contained liquid for immediate absorption thereof.

With this invention, by contrast, an arrangement is provided in the form of an elongated rigid or semi rigid structure for containing a dissolvable packet of gelling material for introduction into, for example, the liquid contained in a suction canister. Because the outer supporting structure is rigid or semi rigid, and contains windows for exposure of the contained envelope of gelling material, the device may be positioned to extend over the entire vertical extent, for example, of the collected fluid. Thus, each increment of the liquid over the vertical extent thereof is immediately, and simultaneously, exposed to the gelling material so that there is no encapsulation or clumping and all increments of the collected fluid are immediately gelled. For this reason, with the invention here, there are no pockets left of partially gelled or ungelled liquids.

Furthermore, the elongated rigid or semi rigid structure may be placed in the canister through an opening in the lid after the canister is filled with body fluids. This eliminates the shortcomings described above.

As a further feature of this invention, it is contemplated that the device or arrangement of the invention may be positioned initially in a suction canister when it is manufactured, or at least prior to any use thereof. Because of this, when liquid is introduced or collected into the suction canister, those portions initially introduced are immediately gelled, and as the container is filled, each increment adjacent the vertical extent of the container and the device positioned therein is immediately gelled upon collection. Because of this, the collected contaminated fluid is immediately contained for subsequent disposal with no problems of liquid spillage and contamination of those handling the canister.

Alternatively, the device of the invention may be inserted by a lab technician after examination of the canister contents for a required analysis of the collected fluid.

Before describing this invention in more detail, it may be well to note that the elongated structure of the invention is arranged to extend over the entire vertical extent, for example, of a suction canister internal cavity, or other aqueous fluid containing container. As such, the arrangement has elongated windows over the vertical extent thereof so as to expose, at each elevation from the bottom surface to the top of the internal cavity of the container, the gelling agent.

Windows are arranged in a variety of configurations, as will be described below, for exposing the packet of gelling material to the liquid collected. It is within the purview of this invention that the elongated arrangement or device of the invention may be placed and fixed internally of the container, as discussed above, for receiving and gelling immediately the collected material. Representative materials which may be used for the containing device of the invention include, for example, rigid and semi rigid thermoplastic materials which may be readily molded in a conventional technique and mass produced for low cost production. The devices may be, for example, oval, triangular, or square in cross section. They may include a press fit cap on one end thereof for receiving the packet of gelling material.

Finally, the gelling material may be contained in an elongated package of material entirely dissolvable in an aqueous containing liquid. The packet may have an adhesive along one side edge for adhering the packet in the desired position to one side edge of the collection container.

The gelling material may be, for example, known gelling material for aqueous liquids, such as sodium polyacrylate as disclosed in the above noted U.S. patents. Commercial products using polyacrylate gelling agents for suction canisters are, for example, RED-Z ™ (Medzam, Ltd., North Tonowanda, N.Y.), and LiquiSorb ® (American Colloid Company, Arlington Heights, Ill.). Other representative gelation materials include highly absorbent products consisting of starch modified with pendent grafted acrylonitrile, acrylamide and sodium acrylate groups such as those disclosed in U.S. Pat. Nos. 3,661,815 and 4,302,369, such materials being available from Grain Processing Corporation, Muscatine, Iowa, under the tradename Water Lock ®.

A preferred gelling agent useful in the device of the invention may be that disclosed and taught in co-pending U.S. Patent application Ser. No. 07/476,869 filed Feb. 7, 1990, which teaches a gelling composition for an aqueous liquid including an ungelated starch which has been reacted with a silane coupling agent. The material may include, for example, a disinfectant for handling contaminated body fluids, as discussed above.

Other objects and advantages of this invention will be apparent from the following description, the accompanying drawings and the appended claims.

DESCRIPTION OF THE DRAWINGS

FIGS. 1 and 2 are somewhat diagrammatic illustrations in elevation of a suction canister indicating a prior art arrangement wherein gelling powder is poured on top of the liquid, as in FIG. 1, or by placing it in the canister before the liquid is added, as in FIG. 2, and indicating the diffusion length for such arrangements.

FIGS. 3 and 4 are somewhat diagrammatic illustrations in elevation of a suction canister wherein the gelling agent is introduced in the form of a packet on top of the liquid, as in FIG. 3, or by placing it in the canister before the liquid is added therein, as in FIG. 4, and indicating the diffusion length for such arrangements.

FIG. 5 is a somewhat diagrammatic indication in elevation of a suction canister illustrating the invention wherein a gelling agent is introduced into a rigid structure which is placed in a liquid filled canister, through the lid, and illustrating the comparative diffusion length of the device as compared to the indications in FIGS. 1, 2, 3 and 4.

FIG. 6 is a somewhat diagrammatic indication in elevation of a suction canister illustrating an additional embodiment of the invention wherein the gelling agent is introduced into an elongated semi-rigid structure affixed to the inside wall of the canister by means of an adhesive stripe before the liquid is introduced, illustrating the diffusion length as compared to the prior art indications in FIGS. 1, 2, 3 and 4.

DETAILED DESCRIPTION OF THE INVENTION

Figure 7:
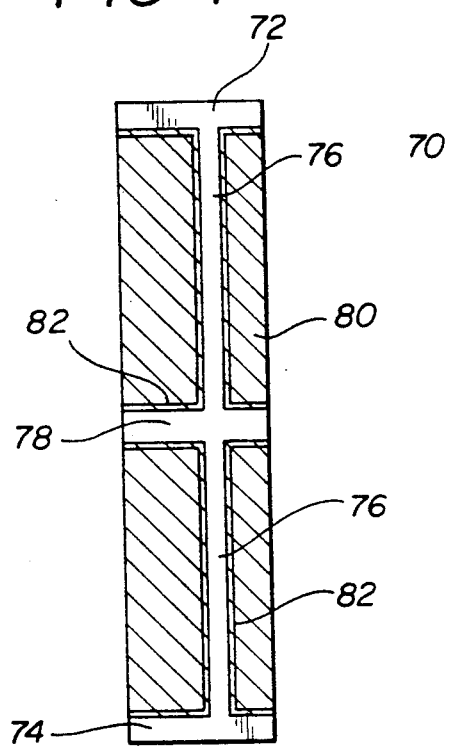
FIG. 7 is an embodiment of one arrangement illustrating the diffusion device of the invention in the form of an elongated structure for containing a material to be dissolved in the aqueous environment of the collected fluids of a suction canister.

Referring to the drawings in which like reference characters refer to like parts throughout the several views thereof, FIGS. 1 and 2 show a diagrammatic illustration of a prior art arrangement for gelling the collected fluid in a suction canister. As can be seen in FIG. 1, canister 10 is a cup shaped container configured in the usual manner of suction canisters with walls 12 diverging from bottom 15 to the top cap 14 thereof. As can be seen in FIG. 1, the prior art arrangement illustrates a gel powder 20 introduced onto the top surface of the contained fluid 13. As further illustrative of the prior art arrangement, the arrow 16 illustrates the diffusion length of the material 20 to extend to the liquid 13 in the bottom of container 10. FIG. 2 illustrates a similar diffusion length when the powder 20 is introduced into the bottom of container 10 prior to use.

FIGS. 3 and 4 are further illustrations utilizing prior art packets. In this case, a packet 22 is introduced onto the top surface of the collected liquid 13. Again, the diffusion length is represented by arrow 16. The length 16 is similar whether the packet 22 is introduced first as in FIG. 4, or after collection as in FIG. 3.

Referring now to FIG. 5, a diagrammatic illustration of a suction canister utilizing one form of arrangement or device of the invention is shown. In this case, again, a conventional suction canister 30 is indicated with walls 40 diverging from bottom 32 of canister 30 and with a cover 34 positioned on the top 35 of canister 30. In this case, a conventional cover arrangement or configuration 34 is shown with an opening 36 for gaining access to the internal cavity of the device and having a cap 38.

As can be seen in FIG. 5, the device 42 of the invention is illustrated in diagrammatic form positioned by being wedged between the circular walls of opening 36 and the bottom surface 32 of suction canister 30.

It should be understood that it is within the purview of this invention to connect a plurality of such canisters in series between the source of the body fluid being collected and the vacuum so that when one canister is filled a subsequent one will take over the containment of the body fluid collected. At any rate, with the arrangement as shown in FIG. 5, the device or arrangement 42 of the invention may be inserted prior to any collection of fluids so that the fluids will be gelled simultaneously with their exposure to device 42 as the collected fluid is introduced into container 30.

Referring further to FIG. 5, arrows 44 indicate the diffusion length of the gelling material from its source 42 to the various components of the liquid 41 collected. It is clear that the diffusion length is much less than is indicated with the arrows 16 in the embodiments shown in FIGS. 1, 2, 3 and 4.

Referring now to FIG. 6, a suction canister 50 is shown similar to 30 shown in FIG. 5 with walls 58 diverging from a base wall 52 to a top 53, closed by a cover 54. Cover 54 has an access opening 57 closed by a cap 56. A device 62 of the invention is shown adhered to the wall 58 by an adhesive 64. The device is adhered prior to use so that the liquid 60 will dissolve the device 62, comprised of a dissolvable starch paper for example, gradually as the canister 60 fills up. Arrows 66 indicate the short diffusion length.

Referring now to FIG. 7, as purely illustrative of one arrangement of gel distribution device of the invention, a device 70 is shown in an elongated configuration with a plurality of windows 80 covered by, for example, a dissolvable material which dissolves for releasing immediately the contained gelling material contained in the device 70 over its entire vertical extent.

As can be seen in FIG. 7, vertical ribs 76 extend from end caps 72, 74 and are joined by horizontal ribs 78 for providing adequate rigid support for the device and support for the dissolvable material 80 which may be, for example, starch paper. The paper may be connected at 82 along the horizontal and vertical extent of ribs 76, 78. At any rate, the starch paper 80 may be adhered along the openings defined by the ribs 76, 78. Once this has taken place, one of end caps 72, 74 may be removed for inserting the actual gelling powder or material prior to the device being inserted into a body of fluid for the gelation thereof.

Figure 8:
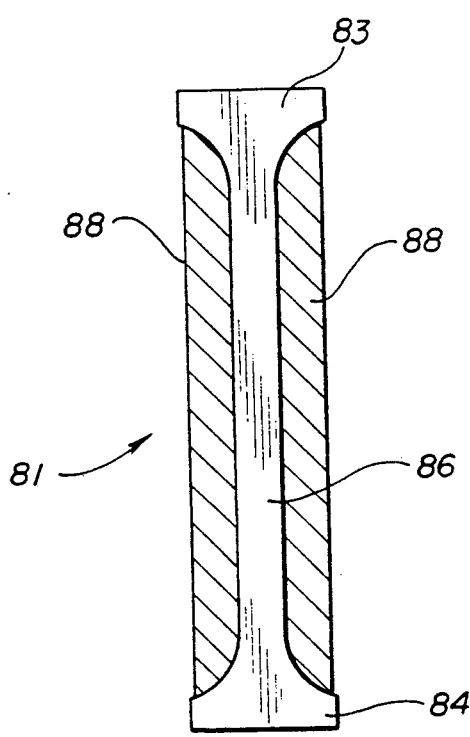
FIG. 8 is a further embodiment of an arrangement illustrating the invention in the form of an elongated container for containing the dissolving material for immediately and simultaneously gelling the contents of a suction canister.

Referring now to FIG. 8, a further embodiment 81 of the invention is shown, again in the form of a rigid or semi-rigid frame 86 having ends 83, 84 with an integral strut or support extending from ends 83, 84. In this case, the dissolvable paper or film material 88 is in the form of a package inserted and supported in the rigid frame 86 with the walls of the package 88 being exposed by the openings in the frame for allowing exposure to the liquid content at the time it is desired to gel the liquid content of a container.

Figure 9A:
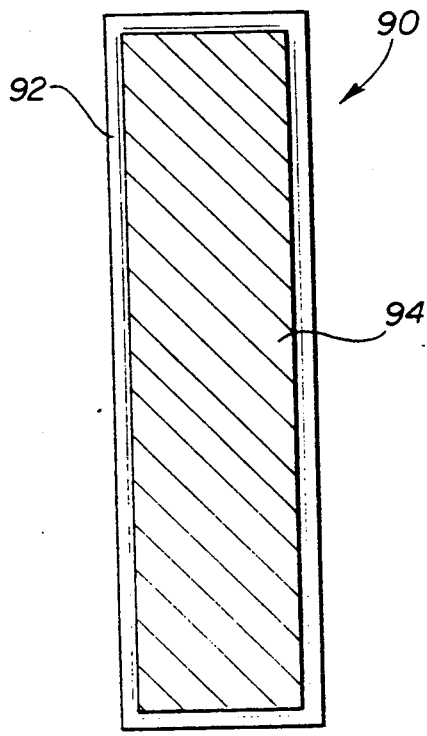
FIG. 9 illustrates a further embodiment of the invention in the form of a soft sided completely dissolvable elongated packet with an adhesive stripe along one side with, and adhered to a flat backing material.
Figure 9B:
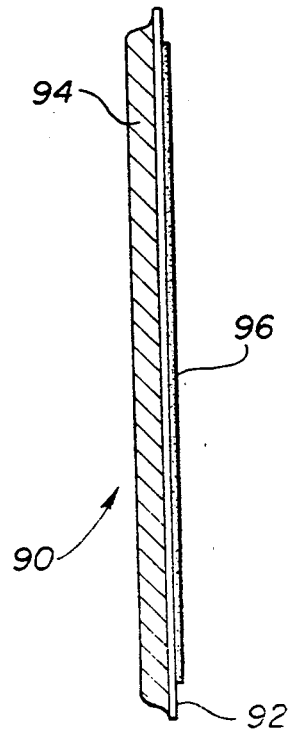
Figure 9C:
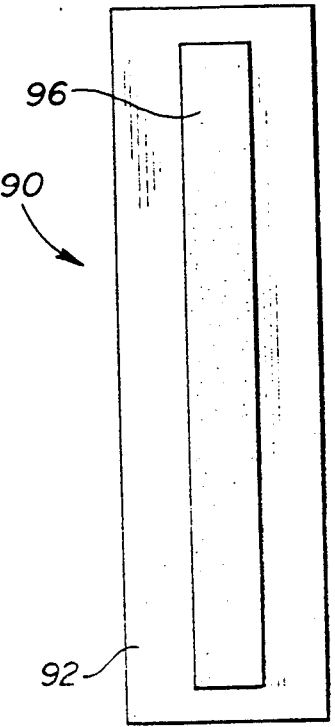

Finally, FIGS. 9a, 9b and 9c show a further embodiment of device 90 which may be positioned in a canister as device 62 is described in FIG. 6. Device 90 comprises a packet 94 of dissolvable material adhered to a backing 92 which may be heavy paper or a light weight cardboard for example. Packet 94 may be starch paper again. On the side of backing 92 opposite packet 94 is an adhesive 94 for adhering device 90 to the vertical walls of a container for collecting liquids to be gelled. Backing 92, also, may be a clear thermoplastic material such as polyethylene or polyvinyl chloride.

In every case, the container holding the gel powder prior to use must be sealed against exposure to moisture prior to use. Preferably, this will be accomplished with moisture proof packaging.

Thus, as will be appreciated from the above, there is provided in accordance with this invention, a device which provides immediate exposure of a gelation material to the entire vertical and/or horizontal extent of a body of fluid so that each increment of the body of fluid is immediately gelled simultaneously. The liquid, which may be a contaminated liquid, is completely contained prior to any danger of spilling of the material.

As discussed above, the device of the invention is comprised of moldable parts which can be mass produced, as will be understood, from a variety of materials and configurations. As will be understood, further, materials should be selected which will provide a degree of resiliency for the purpose of providing the proper wedging positioning of the device 42 of the invention in a suction canister such as that shown in FIG. 5.

While the forms of apparatus herein described constitute preferred embodiments of the invention, it is to be understood that the invention is not limited to these precise forms of apparatus, and that changes may be made therein without departing from the scope of the invention which is defined in the appended claims. For example, whereas, various forms of the device have been shown positioned to extend over the vertical extent of a body of fluid in a suction canister, it will be appreciated that such devices can be configured to extend from wall to wall horizontally across the diameter of such a container. For example, such a device may be positioned midway between the bottom of a container for collecting fluids and the top thereof. Again the diffusion length is reduced substantially.

What is claimed is:

1. A device for evenly distributing gelling material simultaneously over the entire extent of a container of aqueous containing liquid, comprising
   (a) an elongated container having a first end and a second end;
   (b) walls extending from said first end to said second end and defining a chamber;
   (c) a plurality of openings in said walls, said openings extending from a point adjacent said first end to a point adjacent said second end;
   (d) a sheet material for containing a gelation material, said sheet material closing each of said plurality of openings, said sheet material comprised of a material immediately dissolvable sequentially in stages in aqueous containing liquids as it comes in contact with the aqueous containing liquids:
   (e) a gelation material in said chamber, said gelation material responsive to exposure to aqueous containing liquids for the immediate gelation thereof.

2. The device of claim 1, further comprising
   (a) said gelation containing sheet material being in the form of a plurality of pieces with one piece covering one of said openings.

3. The device of claim 1 comprising
   (a) said sheet material containing said gelation material being in the form of an elongated package containing said gelation material; and
   (b) said elongated package being positioned in an aqueous liquid containing chamber.

4. The device of claim 1, further comprising
   (a) said elongated container is circular in cross-section.

5. The device of claim 1, further comprising
(a) said elongated container is square in cross-section.

6. A suction cannister for receiving body fluids from an operation site, comprising
(a) a cannister having circular side walls;
(b) a bottom wall;
(c) a top opening;
(d) said circular side walls extending from said bottom wall to said top opening to define a body fluid collection chamber;
(e) a closure for said top opening;
(f) an access opening in said closure;
(g) a device for evenly distributing gelling material simultaneously over the entire extent of said cannister chamber, said device including
  (1) an elongated container having a first end and a second end;
  (2) walls extending from said first end to said second end;
  (3) a plurality of openings in said walls, said openings extending from a point adjacent said first end to a point adjacent said second end;
  (4) a sheet material for containing a gelation material, said sheet material closing each of said plurality of openings, said sheet material comprised of a material dissolvable in aqueous containing liquids introduced into said suction cannister chamber;
  (5) a gelation material in said device container, said gelation material responsive to exposure to aqueous containing liquids for the gelation thereof; and
(h) said elongated distributing device fixed in said suction cannister chamber with said first end adjacent said bottom wall and said second end adjacent said top opening closure.

7. The device of claim 6, further comprising
(a) said elongated container is circular in cross-section.

8. The device of claim 6, further comprising
(a) said elongated container is square in cross-section.

9. The device of claim 6, further comprising
(a) said gelation containing sheet material being in the form of a plurality of pieces with one piece covering each of said openings.

10. The device of claim 6 further comprising
(a) said sheet material containing said gelation material being in the form of said elongated container containing said gelation material.

11. A device for evenly distributing gelling material simultaneously over the entire extent of a container of aqueous containing liquid, comprising
(a) an elongated container having a first end and a second end;
(b) walls extending from said first end to said second end and defining a chamber;
(c) said walls comprised of a gelation containing sheet material, said sheet material comprised of a material immediately dissolvable sequentially in stages in aqueous containing liquids as it comes into contact with said aqueous containing liquids;
(d) a gelation material in said chamber, said gelation material responsive to exposure to aqueous containing liquids for the immediate gelation thereof;
(e) a flat backing for said container;
(f) one side of said container adhered to said flat backing; and
(g) adhesive adhered to the side of said flat backing opposite said container for adhering said flat backing with the said elongated container attached vertically to the inside wall of an aqueous liquid collection device.

12. The device of claim 11, further comprising
(a) said elongated container is circular in cross-section.

13. The device of claim 11, further comprising
(a) said elongated container is square in cross-section.

* * * * *